US00PP21086P3

(12) United States Plant Patent
Fiselzon

(10) Patent No.: US PP21,086 P3
(45) Date of Patent: Jun. 22, 2010

(54) **DISTINCT ELITE *GYPSOPHILA* PLANT NAMED 'FIORELLO'**

(50) Latin Name: *Gypsophila hybrida*
Varietal Denomination: Fiorello

(75) Inventor: Haim Fiselzon, Doar NA Oshrat 25115 (IL)

(73) Assignee: B I Nursuries, Kibbutz Beit Ha Emek (IL)

( * ) Notice: Subject to any disclaimer, the term of this patent is extended or adjusted under 35 U.S.C. 154(b) by 0 days.

(21) Appl. No.: 12/284,527

(22) Filed: Sep. 22, 2008

(65) Prior Publication Data

US 2010/0077522 P1 Mar. 25, 2010

(51) Int. Cl.
*A01H 5/00* (2006.01)

(52) U.S. Cl. ..... Plt./354

(58) Field of Classification Search ..... Plt./373, Plt./354
See application file for complete search history.

(56) References Cited

U.S. PATENT DOCUMENTS

PP9,257 P 8/1995 Dehan
PP14,504 P2 2/2004 van der Kraan-Zonderland

*Primary Examiner*—Annette H Para
(74) *Attorney, Agent, or Firm*—KK Patents, LLC; Lyn Marantz

(57) ABSTRACT

A new variety of *Gypsophila,* 'Fiorello', is described and illustrated. The new variety exhibits a vigorous growth habit, small flowers, and condensed flowering characteristics combined with upright growth habit. The flowers contain a large number of petals arranged in compound cymes.

1 Drawing Sheet

Latin name of the genus and species of the plant claimed: *Gypsophila hybrida.*

Variety denomination: 'Fiorello'.

BACKGROUND OF THE INVENTION

The invented plant is a hybrid between 2 parental lines. The hybridization was performed by crossing 5 maternal lines with 5 paternal lines as follows.

2) Paternal lines: 'Piccolo' clone 1-clone 5. These are denominated as B-PCC-2.

2) Maternal lines: A parental line denominated as B-M-2.

The plants that were used for the crosses were grown in an insect proof greenhouse in which bees were used for pollination. The enclosed greenhouse contained only 10 plants of *Gypsophila.* Each line was composed of 5 plants. The paternal line was castrated before full aperture of the flower. Pollination was performed over a period of 30 days and seeds were collected from the 5 maternal lines separately. The greenhouse was cooled by air forced vents that were set to operate at 24° C. during the daylight hours. The minimum night temperature was 14° C. Approximately 50 seeds were sown for selection. Seeds were sown in the autumn of the year 2007 and the seedlings were monitored for the following parameters:

Growth habit
Branching habit
Plant height
Plant width
Lateral Branch Length
Lateral Branch diameter
Internode length
Strength
Stem texture Stem color
Flower appearance
Flowering response
Post harvest longevity
Fragrance
Inflorescence length
Inflorescence width
Inflorescence bud morphological character
Flower diameter
Flower depth (height)
Petals/petaloids
Sepals
Peduncles
Pedicles Following observation of the flower characteristics clone number 28 exhibited the desired characteristics as described below in the section entitled Detailed Botanical Description. Ten cuttings were harvested from clone 28 and rooted under mist for further observation and trait stability analysis. In addition, axillary buds from clone 28 were put into tissue culture as routinely used by BI Nursery LTD's laboratory. Following propagation by tissue culture, the plantlets were hardened under mist and planted in 850 ml pots filled with pure Perilite no 2.12 as a soil substrate. Plants were grown to full flowering and monitored along the way for all of the above parameters. These plants were used as mother stock plants for harvesting cuttings as field plants.

FIELD OF THE INVENTION

The present invention comprises breeding of a distinct new variety of *Gypsophila* plant botanically known as *Gypsophila hybrida* denominated as 'Fiorello' variety.

DESCRIPTION OF RELEVANT PRIOR ART

The new variety 'Fiorello' was originated from a cross done in Beit Haemek, Western Galilee, Israel in the year 2006-2007. The male parent is a *Gypsophila* variety designated as 'Piccolo clone' 1-clone 5. These are denominated as B-PCC-2. The female parent is a *Gypsophila* variety denominated as B-M-2. 'Fiorello' was discovered by a selection of seeds that were germinated from the cross hybridization between B-M-2 and B-PCC-2.

'Fiorello' is a distinct *Gypsophila* hybrid that originates from a cross between the parental lines B-M-2 and B-PCC-2 in a controlled breeding program. Both parental lines are hybrids that have been developed in BI Nurseries, Beit Haemek, Western Galilee, Israel and have not been patented and are not disclosed in the public domain. Of the commercial varieties known to the inventor the closest one that can be compared to 'Fiorello' is 'Blancavievens', disclosed in U.S. Plant Pat. No. 14,504 P2.

In a side-by-side comparison between 'Blancavienvens' and 'Fiorello' conducted in Kibbutz Beit Haemek in the Western Galilee, Israel, major morphological and physiological differences were observed. 'Fiorello''s inflorescence is longer, wider and fuller with more flowers per branch than 'Blancavienvens'. There are also distinct differences between 'Blancavienvens' and 'Fiorello' with respect to the growth habit. Under Israeli winter conditions 'Fiorello' grew significantly faster and flowered earlier than 'Blancavienvens'. One major difference between the two varieties is arrangement and spread of lateral branches. While lateral branches of 'Blancavienvens' are mostly upright, 'Fiorello' is distinct in having a defused and widely branching style. In addition the 'Blancavienvens' flowers are devoid of stamens; 'Fiorello' flowers typically have 4 stamens per flower bud. The number of flowers per plant is another major difference between the two varieties, while 'Blancavienvens' has approximately 300 flowers, we counted approximately double number of flowers, 600 flowers, in 'Fiorello'.

Another variety that 'Fiorello' was compared to is 'Magic Golan' described in U.S. Plant Pat. No. 9,257. Data was collected in a side-by-side comparison performed in Beit Haemek during the winter of 2006-2007. A very distinct difference between the two varieties is the number of flower per plant. While 'Magic Golan' produced approximately 1000 flowers per plant, 'Fiorello' produced about 600 flowers. Another critical difference is the time of flower appearance. While 'Magic Golan' appears as a neutral daylight flowering plant, 'Fiorello' requires at least 13-14 hrs of light for flowering.

SUMMARY OF THE INVENTION

The following traits have been repeatedly observed and are determined to be the unique characteristics of 'Fiorello'. These characteristics in combination distinguish 'Fiorello' as a new and distinct variety:

Flower characteristics:

The flower size belongs to the small class of *Gypsophila* varieties but in that class it is considered larger than most. 'Fiorello' is between 6 and 7 mm in diameter which is larger than existing small flower types of *Gypsophilia* such as 'Million Stars' which is 4 to 5 mm and 'Bambino' which is 5-6 mm. 'Fiorello' is smaller than the large flower *Gypsophilia* varieties such as 'Perfecta' which is 11 mm in diameter. The inflorescence is composed of a relatively large number of flowers in a highly branched arrangement. This new variety exhibits a vigorous growth habit and flowers under long day conditions of a minimum of 13 hours of light. In addition, the number of petals of 'Fiorello' is among the largest within the group of small *Gypsophilia* flowers averaging 31 petals compared to 18 petals for 'Million Stars', 25 petals for 'Bambino', and 12 petals for 'Piccolo'. All of the above measurements were performed in the spring of the year 2007 in plastic covered greenhouses in Kibbutz Beit Haemek in the Western Galilee, Israel.

BRIEF DESCRIPTION OF THE DRAWING

The color photograph of *Gypsophila* variety 'Fiorello' illustrates the overall appearance of the inflorescence. In this photograph, the colors are as true as it is reasonably possible to obtain in color reproduction of this type. A better description of the colors is cited in the detailed botanical description section (i) of this plant application.

DETAILED BOTANICAL DESCRIPTION

In the following description, color references are made to The Royal Horticultural Society Colour Chart, 2001 Edition, except where general terms of ordinary dictionary significance are used. The aforementioned photograph, following observations and measurements describe 0.5 year old plants grown as cut flowers during the winter of 2007 in location Kibbutz Beit Haemek, Israel, in a polyethylene covered greenhouse with day temperatures of about 25° C. and night temperatures of about 14° C.

Botanical classification: *Gypsophila hybrida* variety 'Fiorello'.

Commercial classification: Cut flower *Gypsophila.*

Parentage:

*Paternal lines.*—'Piccolo' clone 1-clone 5.

*Maternal lines.*—B-M-2.

Propagation:

*Type.*—By cuttings.

*Time to initiate roots.*—Summer: About 18-25 days at a temperature of 26° C. Winter: About 26-30 days at a temperature of 18° C.

*Root description.*—Highly branched roots.

Plant description:

*Appearance.*—Perennial cut flower. Stems upright; broadly inverted triangular form. Freely flowering; white-colored flowers with numerous petals per flower arranged in compound cymes.

*Growth habit.*—High.

*Branching habit.*—Normal.

*Plant height.*—About 120 cm.

*Plant width.*—About 90 cm.

*Lateral branch length.*—About 80 cm.

*Lateral branch diameter.*—About 2.5-3 mm.

*Internode length.*—About 6-7 cm.

*Strength.*—High.

*Stem texture.*—Glabrous.

*Stem color.*—Green.

Foliage description:

*Arrangement.*—Opposite; sessile.

*Shape.*—Narrowly elliptic to narrowly lanceolate.

*Apex.*—Acute.

*Base.*—Cuneate.

*Margin.*—Entire.

*Length.*—About 6 cm.

*Width.*—About 0.65 cm.

*Texture.*—Glabrous; slightly leathery.

*Venation pattern.*—Parallel.

*Color.*—Young leaves, upper surface: 189B. Young leaves, lower surface: 189B. Fully expanded leaves, upper surface: 189B. Fully expanded leaves, lower surface: 137B. Venation, upper surface: 189B. Venation, lower surface: 143A.

Flowering description:

*Appearance.*—Upright compound cymes with numerous many-petalled white-colored flowers, flowers rotate; numbering about 600 flowers per plant. Flowers face upright to slightly outwardly.

*Flowering response.*—The conditions in which the plants were grown (Western Galilee, Israel) the day length was supplemented with incandescent 150 watts light bulbs spaced at 3×3 meters, 1 meter above the plants. The total hours of lighting (including the natural daylight) amounted to 16 hours/24 hours. Under these conditions 100% of the plants flowered 60 days after being planted in the field.

*Post.*—Production longevity.—14 days.

*Fragrance.*—Slight sweet fragrance.

*Inflorescence length.*—About 30 cm.

*Inflorescence width.*—About 45 cm.

*Inflorescence bud.*—Shape: convex. Length: About 4.5 mm Diameter: About 6.5 mm. Color: brilliant white 157C.

*Flower diameter.*—About 6.5 mm.

*Flower depth* (*height*).—About 4 mm.

*Petals/petaloids.*—Quantity per flower: About 30. Shape: oblanceolate. Apex: recurved.

*Base.*—Attenuate. Margin: Entire. Length: About 3.6 mm. Width: About 1.8 mm. Texture: Smooth. Color: When opening, upper and lower surfaces: Close to 155D; towards the base155D; Mature, upper and lower surfaces: Close to 155B; towards the base, 155B; color becoming closer to 155B; with development.

*Sepals.*—Quantity per flower: About 5. Shape: cup. Apex: acute. Base: Cuneate. Margin: Entire. Length: About 1.5 min. Width: About 1 mm. Color: Immature and mature, upper surface: 140A. Immature and mature, lower surface: 137B.

*Peduncle.*—Strength: Strong. Length: About 1.8 cm. Diameter: About 0.9 mm. Angle: About 35° from vertical. Texture: Smooth. Color: 143A.

*Pedicels.*—Strength: strong. Length: About 10 mm. Diameter: About 0.3 min. Angle: About 35° from vertical. Texture: Smooth. Color: 143A.

*Reproductive organs.*—Stamens: 4, all transformed into petaloids. Pistils: Quantity per flower: About two. Style length: About 2.2 mm. Style color: 157B to 157C. Pistil length: About 2.5 mm. Stigma color: 157C to 157D. Ovary color: 143A.

*Seed/fruit development.*—None.

Disease/pest resistance: none.

The invention claimed is:

1. A distinct variety of *Gypsophila* plant named 'Fiorello' as described and illustrated.

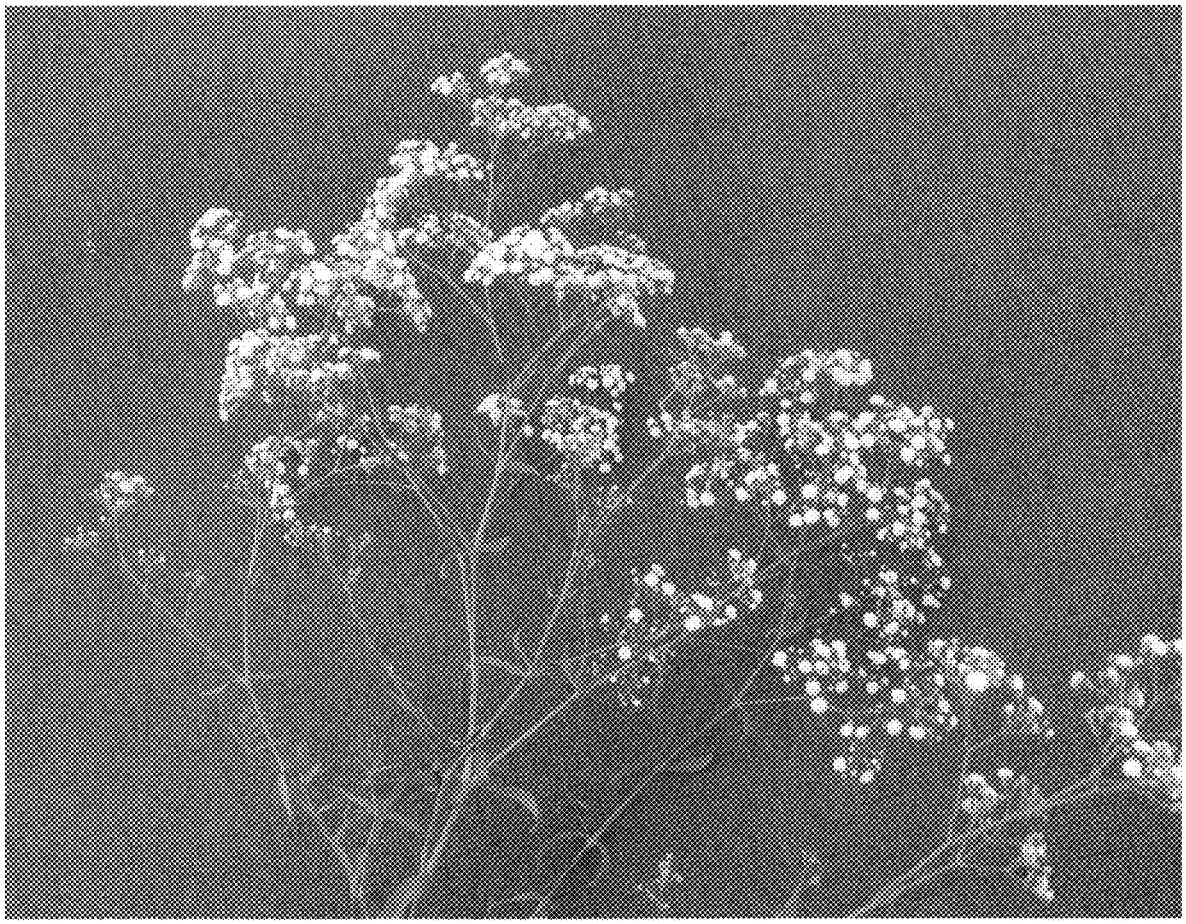

* * * * *